United States Patent [19]

Kagara et al.

[11] Patent Number: 5,523,410
[45] Date of Patent: Jun. 4, 1996

[54] INTERMEDIATE FOR SYNTHESIS AND PRODUCTION OF AMINO ACID DERIVATIVE

[75] Inventors: Kooji Kagara, Mino; Nobutaka Kawai, Osaka; Koji Machiya, Kobe; Tetsuo Furutera, Takarazuka; Takashi Nakamura; Hiroki Omori, both of Nishinomiya, all of Japan

[73] Assignee: Fujisawa Pharmaceutical Co., Ltd., Osaka, Japan

[21] Appl. No.: 360,683

[22] PCT Filed: Jun. 28, 1993

[86] PCT No.: PCT/JP93/00885

§ 371 Date: Jan. 3, 1995

§ 102(e) Date: Jan. 3, 1995

[87] PCT Pub. No.: WO94/01409

PCT Pub. Date: Jan. 20, 1994

[30] Foreign Application Priority Data

Jul. 2, 1992 [JP] Japan ................................. 4-175806
Dec. 2, 1992 [JP] Japan ................................. 4-323483

[51] Int. Cl.⁶ ..................... C07D 233/64; C07D 413/12

[52] U.S. Cl. ..................... 548/338.1; 544/122; 544/370; 546/146; 546/168; 546/210; 546/275.1; 546/274.7; 546/274.4; 548/518; 548/364.1; 548/200; 548/215

[58] Field of Search ....................... 548/338.1; 544/122; 514/400, 235.8

[56] References Cited

U.S. PATENT DOCUMENTS 5,142,048 8/1992 Hemmi et al. ..................... 544/172

FOREIGN PATENT DOCUMENTS 0528629 2/1993 European Pat. Off. ......... C07K 5/06

OTHER PUBLICATIONS

Morrison, R. T. et al., Organic Chemistry, 5th ed., Allyn and Bacon, Inc., Boston, 1987.

Primary Examiner—Johann Richter
Assistant Examiner—Laura R. Cross
Attorney, Agent, or Firm—Oblon, Spivak, McClelland, Maier & Neustadt

[57] ABSTRACT

The present invention relates to synthetic intermediates useful for preparing amino acid derivatives possessing renin-inhibitory activity, and to processes for preparing the amino acid derivatives using the synthetic intermediates.

3 Claims, No Drawings

INTERMEDIATE FOR SYNTHESIS AND PRODUCTION OF AMINO ACID DERIVATIVE

This is a 371 of PCT/JP93/00885 filed Jun. 28, 1993.

TECHNICAL FIELD

The present invention relates to a novel synthetic intermediate for preparing amino acid derivatives possessing renin-inhibitory activity, and to processes for preparing the amino acid derivatives using said synthetic intermediate.

BACKGROUND ART

The amino acid derivative of the formula

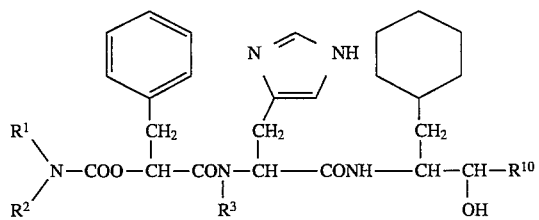

wherein $R^1$, $R^2$, $R^3$, and $R^{10}$ are as defined later, is known to have renin-inhibitory activity and to be useful for the treatment of hypertensions such as essential hypertension, renal hypertension, and malignant hypertention, heart failure, and the like. EP-A-300189 discloses the following synthetic method For preparing said compound.

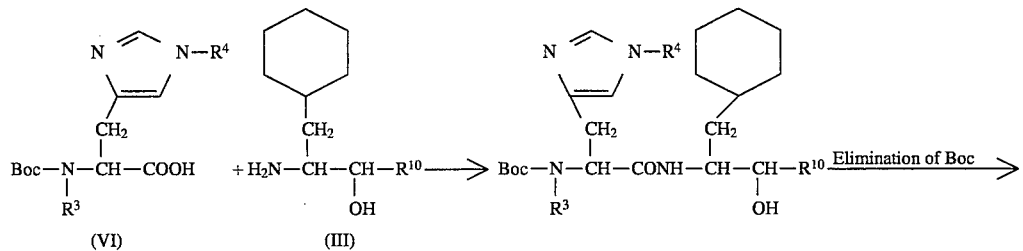

(Boc: tert-butoxycarbonyl)

wherein $R^1$, $R^2$, $R^3$, $R^4$, and $R^{10}$ are as defined later.

The aforementioned method is, however, not entirely satisfactory as an industrial preparation method in that a starting material (VI) is relatively expensive and the total yield of the processes as a whole is as low as about 40–50%, thus rendering preparation cost of the object final product amino acid derivatives (I) considerably high.

DISCLOSURE OF THE INVENTION

Accordingly, an object of the present invention is to solve such problems of the conventional method by providing industrially advantageous processes for preparing the amino acid derivatives (I) at high yields from a less expensive starting material.

Another object of the present invention is to provide an intermediate for the preparation of the amino acid derivatives (I), which is synthesized from a less expensive starting material.

The present inventors have found that the amino acid derivatives (I) can be obtained at high yields from a less expensive starting material via a compound (II) which is a novel intermediate to be mentioned later, and completed the present invention.

Accordingly, the present invention relates to a compound (II) of the formula

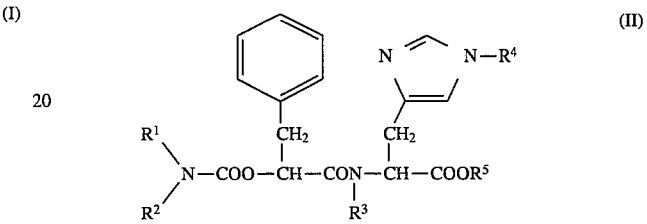

wherein $R^1$ is lower alkyl which may be substituted by a substituent selected from the group consisting of acyl, hydroxyl, lower alkoxy, aryl, lower alkylthio and a group of the formula

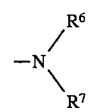

(wherein $R^6$ is hydrogen or acyl, and $R^7$ is hydrogen or lower alkyl); aryl; or amino which may be substituted by substituent(s) selected from the group consisting of lower alkyl and acyl;

$R^2$ is hydrogen or lower alkyl; or $R^1$ and $R^2$ together with the attached nitrogen atom form a heterocyclic group which may be substituted by substituent (s) selected from the group consisting of lower alkyl, hydroxy(lower)alkyl, lower alkoxy(lower)alkyl, acyl(lower)alkyl, oxo and acyl;

$R^3$ is hydrogen or lower alkyl;

$R^4$ is hydrogen or an N-protective group; and $R^5$ is hydrogen or a carboxy-protective group; and to a salt thereof.

According to the present invention, the compound (I) of the formula

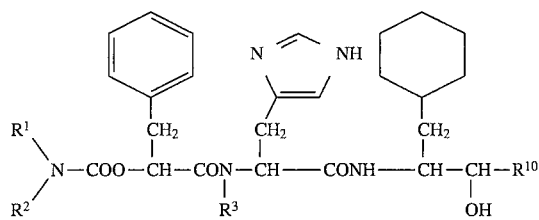

wherein $R^{10}$ is lower alkyl, and $R^1$, $R^2$, and $R^3$ are as defined above, and a salt thereof can be prepared by reacting a compound (IIa) of the formula

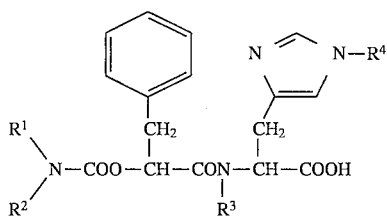

wherein $R^1$, $R^2$, $R^3$, and $R^4$ are as defined above, or its reactive derivative at the carboxyl group or a salt thereof with a compound (III) of the formula

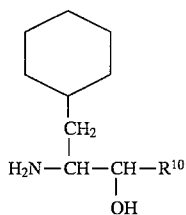

wherein $R^{10}$ is as defined above, or its reactive derivative at the amino group or a salt thereof, followed by elimination of the N-protective group, if necessary (hereinafter this process is to be referred to as Process a).

According to the present invention, the compound (I) and a salt thereof can be prepared by reacting a compound (IV) of the formula

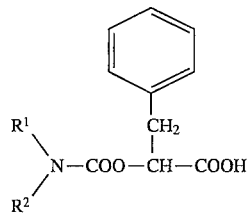

wherein $R^1$ and $R^2$ are as defined above, or its reactive derivative at the carboxyl group or a salt thereof with a compound (V) of the formula

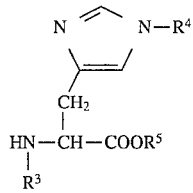

wherein $R^3$, $R^4$, and $R^5$ are as defined above, or its reactive derivative at the amino group or a salt thereof to give a compound (II) of the formula

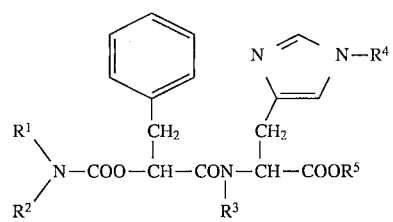

wherein $R^1$, $R^2$, $R^3$, $R^4$, and $R^5$ are as defined above, or a salt thereof, and reacting the obtained compound (II) or its reactive derivative at the carboxyl group or a salt thereof with a compound (III) of the formula

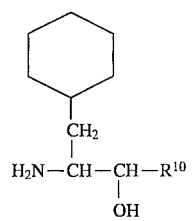

wherein $R^{10}$ is as defined above, or its reactive derivative at the amino group or a salt thereof, followed by elimination of the N-protective group, if necessary (hereinafter this process is to be referred to as Process b).

According to the present invention, the compound (I) and a salt thereof can be prepared by reacting a compound (IV) of the formula

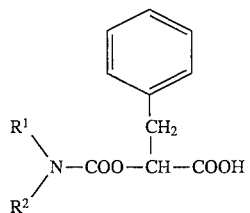

wherein $R^1$ and $R^2$ are as defined above, or its reactive derivative at the carboxyl group or a salt thereof with a compound (Va) of the formula

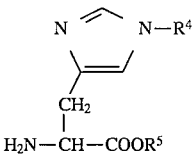

wherein $R^4$ and $R^5$ are as defined above, or its reactive derivative at the amino group or a salt thereof to give a compound (IIb) of the formula

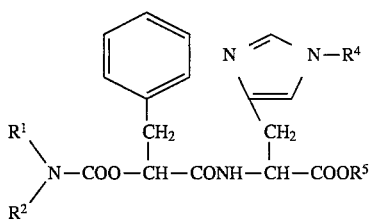

(IIb)

wherein $R^1$, $R^2$, $R^4$, and $R^5$ are as defined above, or a salt thereof, subjecting said compound or its salt to lower alkylation reaction to give a compound (IIc) of the formula

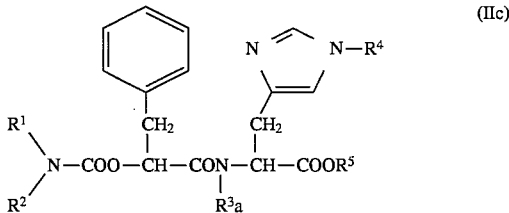

(IIc)

wherein $R^3a$ is lower alkyl, and $R^1$, $R^2$, $R^4$, and $R^5$ are as defined above, or a salt thereof, and further reacting the obtained compound (IIc) or its reactive derivative at the carboxyl group or a salt thereof with a compound (III) of the formula

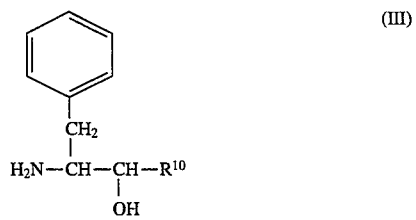

(III)

wherein $R^{10}$ is as defined above, or its reactive derivative at the amine group or a salt thereof, followed by elimination of the N-protective group, if necessary (hereinafter this process is to be referred to as Process c).

In the above and subsequent description of the present specification and claims, suitable examples of the various definitions to be included within the scope of the invention are as follows.

The term "lower" means a group having 1 to 7 carbon atom(s), unless otherwise specified.

Suitable "lower alkyl" may be straight or branched, and includes, for example, methyl, ethyl, propyl, isopropyl, butyl, isobutyl, tert-butyl, pentyl, isopentyl, hexyl, methylhexyl, and heptyl.

Examples of suitable "acyl" and "acyl" moiety of "acyl(lower)alkyl" include a group of the formula

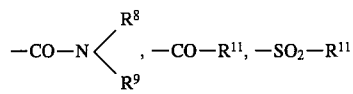

[wherein $R^3$ and $R^9$ are each hydrogen, aryl, cyclo(lower)alkyl, heterocyclic group, or lower alkyl which may be substituted by a substituent selected from tile group consisting of lower alkoxycarbonyl, lower alkoxy, aryl and heterocyclic group, or $R^8$ and $R^9$ together with the attached nitrogen atom form a heterocyclic group which may be substituted by lower alkyl, and $R^{11}$ is aryl, cyclo(lower)alkyl, lower alkyl optionally substituted by a substituent selected from the group consisting of lower alkoxy and mono- or di(lower)alkylamino, or lower alkoxy optionally substituted by a substituent selected from the group consisting of lower alkanoyl and aryl], and amino-protected or unprotected amino acid residue.

Suitable "aryl" may be phenyl, naphthyl, tolyl, xylyl, mesityl, or cumenyl, with preference given to phenyl.

Suitable "cyclo(lower)alkyl" is $C_3$–$C_7$ cycloalkyl, for example, cyclopropyl, cyclobutyl, cyclopentyl, or cyclohexyl.

Suitable "heterocyclic group" for $R^8$ and $R^9$ and one as a substituent on lower alkyl for $R^8$ and $R^9$ may include saturated or unsaturated, monocyclic or polycyclic one containing at least one hereto atom such as nitrogen atom, oxygen atom or sulfur atom, which is preferably an N-, O- and/or S-containing 5 or 6-membered heterocyclic group, with most preference given to morpholino, pyridyl, and thiazolyl.

Suitable "lower alkoxy" and "lower alkoxy" moiety of "lower alkoxycarbonyl" may be straight or branched one such as methoxy, ethoxy, propoxy, isopropoxy, butoxy, isobutoxy, tert-butoxy, pentyloxy, and hexyloxy, or which more preferable one is $C_1$–$C_4$ alkoxy.

Suitable "heterocyclic group" formed by $R^8$, $R^9$ and the attached nitrogen atom is, for example, morpholino, thiomorpholino, its 1-oxide or 1,1-dioxide, pyrrolidin-1-yl, pyrazolidin-1-yl, piperidino, piperazin-1-yl, pyrrolin-1-yl, thiazolidin-3-yl, its 1-oxide or 1,1-dioxide, oxazolidin-3-yl, perhydropyridazin-1-yl, 1,4-dihydropyridin-1-yl, 1,2,3,6-tetrahydropyridin- 1-yl, 1,2,3,4-tetrahydroisoquinolin-2-yl, 1,2,3,4-tetrahydroquinolin-1-yl, hexamethyleneimino, or 1,4-diazabicyclo[4.3.0]nonan-4-yl.

Suitable "mono- or di(lower)alkylamino" may be methylamino, ethylamino, propylamino, isopropylamino, butylamino, isobutylamino, dimethylamino, methylethylamino, methylisopropylamino, or diethylamino.

Suitable "lower alkanoyl" may be formyl, acetyl, propionyl, butyryl, isobutyryl, valeryl, isovaleryl, pivaloyl, or 4-methylvaleryl.

Suitable "amino-protected or unprotected amino acid residue" may be glycyl, alanyl, β-alanyl, valyl, leucyl, isoleucyl, histidyl, prolyl, seryl, threonyl, cystyl, phenylalanyl, aspartyl, glutamyl, or tryptophyl, each amino group of which may be protected by N-protective group such as substituted or unsubstituted lower alkanoyl [e.g. formyl, acetyl, propionyl, trifluoroacetyl], phthaloyl, lower alkoxycarbonyl [e.g. tert-butoxycarbonyl, tert-amyloxycarbonyl], substituted or unsubstituted aralkyloxycarbonyl [e.g. benzyloxycarbonyl, p-nitrobenzyloxycarbonyl], substituted or unsubstituted arene-sulfonyl [e.g. benzenesulfonyl, tosyl], nitrophenylsulfenyl, or aralkyl [e.g. trityl, benzyl].

Preferred examples of the above-mentioned acyl group are lower alkanoyl [e.g. formyl, acetyl, propionyl, butyryl, isobutyryl, valeryl, isovaleryl, pivaloyl, 4-methylvaleryl], mono- or di(lower)alkylamino(lower)alkanoyl [e.g. methylaminoacetyl, methylaminopropionyl, dimethylaminobutyryl], lower alkoxy(lower)alkanoyl [e.g. methoxyacetyl, methoxypropionyl, ethoxypropionyl], aroyl [e.g. benzoyl, toluoyl], cyclo(lower)alkylcarbonyl [e.g. cyclopropylcarbonyl, cyclobutylcarbonyl, cyclopentylcarbonyl, cyclohexylcarbonyl], amino-protected or unprotected amino acid residue [e.g. glycyl, benzoylglycyl, t-butoxycarbonylglycyl, t-butoxycarbonylleucyl, acetylleucyl, t-butoxycarbonylhistidyl], carbamoyl, mono- or di(lower)alkylcarbamoyl [e.g. methylcarbamoyl, ethylcarbamoyl, propylcarbamoyl, isopropylcarbamoyl, butylcarbamoyl, pentylcarbamoyl, isobutylcarbamoyl, tert-butylcarbamoyl, dimethylcarbamoyl, diethylcarbamoyl, methylethylcarbamoyl, methylisopropylcarbamoyl, methylisobutylcarbamoyl], heterocyclic(lower)-alkylcarbamoyl [e.g. picolylcarbamoyl, pyridylethylcarbamoyl, thiazolylmethylcarbamoyl, morpholinomethylcarbamoyl, morpholinoethylcarbamoyl], N-heterocyclic(lower)alkyl-N-lower alkylcarbamoyl [e.g. N-picolyl-N-methylcarbamoyl, N-pyridylethyl-N-methylcarbamoyl, N-morpholinomethyl-N-ethylcarbamoyl, N-morpholinoethyl-N-methylcarbamoyl], aryl(lower)alkylcarbamoyl [e.g. benzylcarbamoyl, phenethycarbamoyl, benzhydrylcarbamoyl], N-aryl(lower)alkyl-N-lower alkylcarbamoyl [e.g. N-benzyl-N-methylcarbamoyl, N-phenethyl-N-methylcarbamoyl, N-phenethyl-N-ethylcarbamoyl], N-aryl-N-lower alkylcarbamoyl [e.g. N-phenyl-N-methylcarbamoyl], lower alkoxycarbonyl(lower)alkylcarbamoyl [e.g. methoxycarbonylmethylcarbamoyl, ethoxycarbonylmethylcarbamoyl, ethoxycarbonylethylcarbamoyl], lower alkoxy(lower)alkylcarbamoyl [e.g. methoxymethylcarbamoyl, methoxyethylcarbamoyl, ethoxypropylcarbamoyl], aroylcarbamoyl [e.g. benzoylcarbamoyl, toluoylcarbamoyl], heterocycliccarbamoyl [e.g. pyridylcarbamoyl, morpholinocarbamoyl, thiazolylcarbamoyl], N-heterocyclic-N-lower alkylcarbamoyl [e.g. N-pyridyl-N-methylcarbamoyl, N-thiazolyl-N-methylcarbamoyl], heterocycliccarbonyl, preferably N-containing heterocyclic-N-ylcarbonyl which may be substituted by lower alkyl [e.g. morpholinocarbonyl, thiomorpholinocarbonyl, piperidinocarbonyl, 4-methyl-1-piperazinylcarbonyl, 1,2,3,6-tetrahydro-1-pyridylcarbonyl], lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl], mono(or di or tri)halo(lower)alkoxycarbonyl [e.g. iodoethoxycarbonyl, dichloroethoxycarbonyl, trichloroethoxycarbonyl, trifluoromethoxycarbonyl], hydroxy(lower)alkoxycarbonyl [e.g. hydroxymethoxycarbonyl, hydroxyethoxycarbonyl, hydroxypropoxycarbonyl, hydroxybutoxycarbonyl], aryl(lower)alkoxycarbonyl [e.g. benzyloxycarbonyl, phenethyloxycarbonyl, 4-nitrobenzyloxycarbonyl, trityloxycarbonyl, benzhydryloxycarbonyl], lower alkenyloxycarbonyl [e.g. vinyloxycarbonyl, allyloxycarbonyl], lower alkanoyl(lower)alkoxycarbonyl [e.g. acetylmethoxycarbonyl, propionylmethoxycarbonyl, acetylethoxycarbonyl], lower alkylsulfonyl [e.g. mesyl, ethylsulfonyl, propylsulfonyl, isopropylsulfonyl, butylsulfonyl, isobutylsulfonyl, tert-butylsulfonyl, pentylsulfonyl, hexylsulfonyl], and arylsulfonyl [e.g. phenylsulfonyl, tosyl].

Suitable "lower alkylthio" may be a straight or branched one such as methylthio, ethylthio, propylthio, isopropylthio, butylthio, isobutylthio, tert-butylthio, pentylthio, or hexylthio, of which more preferable one is $C_1$–$C_4$ alkylthio.

Suitable "heterocyclic group" formed by $R^1$, $R^2$ and the attached nitrogen atom can be referred to the ones formed by $R^8$, $R^9$ and the attached nitrogen atom as exemplified above.

Suitable "hydroxy(lower)alkyl" may be hydroxymethyl, hydroxyethyl, hydroxypropyl, hydroxyisopropyl, or hydroxybutyl.

Suitable "lower alkoxy(lower)alkyl" may be methoxymethyl, ethoxymethyl, methoxyethyl, ethoxyethyl, or methoxypropyl.

Suitable "N-protective group" may be substituted or unsubstituted lower alkanoyl [e.g. formyl, acetyl, propionyl, trifluoroacetyl], phthaloyl, lower alkoxycarbonyl [e.g. tert-butoxycarbonyl, tert-amyloxycarbonyl], substituted or unsubstituted aralkyloxycarbonyl [e.g. benzyloxycarbonyl, p-nitrobenzyloxycarbonyl], substituted or unsubstituted arenesulfonyl [e.g. benzenesulfonyl, tosyl], nitrophenylsulfenyl, or aralkyl [e.g. trityl, benzyl].

Suitable "carboxy-protective group" may be lower alkyl such as methyl, ethyl, propyl, isopropyl, butyl, sec-butyl, isobutyl, tert-butyl, pentyl, neopentyl, and hexyl, or optionally substituted aryl(lower)alkyl, such as mono- or di- or tri-phenyl(lower)alkyl which may be substituted by nitro (e.g. benzyl, 4-nitrobenzyl, benzhydryl, trityl).

Suitable "lower alkylene" may be a straight or branched one such as methylene, ethylene, trimethylene, tetramethylene, pentamethylene, hexamethylene, propylene, methylmethylene, ethylmethylene, and propylmethylene, of which more preferable one is $C_1$–$C_4$ alkylene and the most preferable ones are methylene, ethylene, trimethylene, tetramethylene and methylmethylene.

Suitable salts include organic acid addition salts [e.g. formate, acetate, trifluoroacetate, maleate, tartrate, methanesulfonate, benzenesulfonate, toluenesulfonate], inorganic acid addition salts [e.g. hydrochloride, hydrobromide, sulfate, phosphate], and salt with amino acid [e.g. aspartic acid salt, glutamic acid salt]. When a compound includes a carboxyl group, suitable salts include, in addition to the aforementioned acid addition salts, base salts such as alkali metal salt [e.g. sodium salt, potassium salt], alkaline earth metal salt [e.g. calcium salt, magnesium salt], ammonium salt, and organic base salt [e.g. trimethylamine salt, triethylamine salt, pyridine salt, picoline salt, dicyclohexylamine salt, N,N'-dibenzylethylenediamine salt].

Preferable examples of $R^1$ to $R^5$ are given in the following.

$R^1$ is preferably lower alkyl substituted by a group of the formula

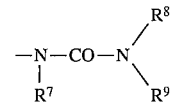

wherein $R^7$ is hydrogen or lower alkyl, and $R^8$ and $R^9$ together with the attached nitrogen atom form a heterocyclic group which may be substituted by lower alkyl; $R^2$ is lower alkyl; $R^3$ is hydrogen or lower alkyl; $R^4$ is hydrogen or an N-protective group; and $R^5$ is hydrogen or lower alkyl.

Particularly preferable examples of the compound (II) are: $N^\alpha$-[2(S)-[N-methyl-N-[2-{N-(morpholinocarbonyl)-N-methylamino}ethyl]aminocarbonyloxy]-3-phenylpropionyl]-$N^{im}$-trityl-L-histidine and a salt thereof, and $N^\alpha$-[2(S)-[N-methyl-N-[2-{N-(morpholinocarbonyl)-N-methylamino}ethyl]aminocarbonyloxy]-3-phenylpropionyl]-$N^\alpha$-methyl-$N^{im}$-trityl-L-histidine and a salt thereof.

The compound (II) may comprise one or more stereoisomers due to asymmetric carbon. Such isomers and mixtures thereof are encompassed in the scope of the invention.

The compound (II) of the present invention is useful as an intermediate for synthesizing the amino acid derivatives (I). The processes for preparing the amino acid derivatives (I) via the compound (II) is explained in the following.

Process a

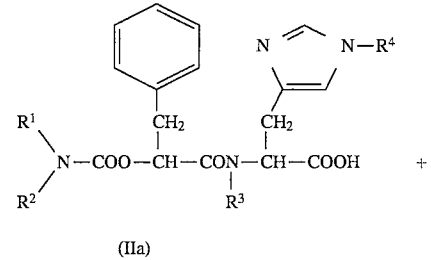

(IIa)

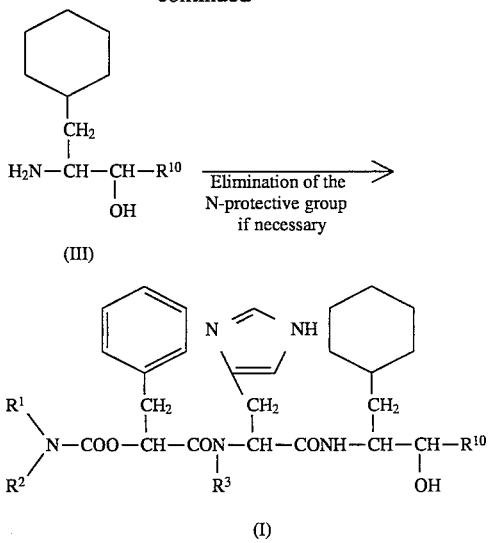

wherein $R^1$, $R^2$, $R^3$, $R^4$, and $R^{10}$ are as defined above.

The compound (I) or its salt can be prepared by reacting a compound (IIa) or its reactive derivative at the carboxyl group or a salt thereof with a compound (III) or its reactive derivative at the amino group or a salt thereof, followed by elimination of the N-protective group, if necessary. Suitable reactive derivative at the carboxyl group of the compound (IIa) includes acid halide, acid anhydride, activated amide, and activated ester. Suitable examples of the reactive derivative are acid chloride; acid azide; mixed acid anhydride with acid such as substituted phosphoric acid [e.g. dialkylphosphoric acid, phenylphosphoric acid, diphenylphosphoric acid, dibenzylphosphoric acid, halogenated phosphoric acid], dialkylphosphorous acid, sulfurous acid, thiosulfuric acid, sulfuric acid, sulfonic acid [e.g. methanesulfonic acid], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid], or aromatic carboxylic acid [e.g. benzoic acid], symmetrical acid anhydride, activated,amide with imidazole, 4-substituted imidazole, dimethylpyrazole, triazole or tetrazole or activated ester [e.g. cyanomethyl ester, methoxymethyl ester, dimethyliminomethyl [$(CH_3)_2N^+$=CH—]ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester], and ester with N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole]. The reactive derivative can be selected optionally from those exemplified, according to the kind of the compound (IIa) to be used.

Suitable reactive derivative at the amino group of the compound (III) includes Schiff's base type imino and its tautomeric enamine type isomer formed by the reaction of the compound (III) with a carbonyl compound such as aldehyde or ketone; silyl derivatives formed by the reaction of the compound (III) with a silyl compound such as bis(trimethyl-silyl)acetamide, mono(trimethylsilyl)acetamide, bis(trimethylsilyl)urea, or combination of 1,1,1,3,3,3-hexamethyldisilazane and trimethylsilyl chloride; and derivatives formed by the reaction of the compound (III) with phosphorus trichloride or phosgene.

The reaction is usually carried out in a conventional solvent such as water, alcohol [e.g. methanol, ethanol], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may be used in mixture with water.

In this reaction, when the compound [IIa] is used in a free acid form or its salt form, the reaction is preferably carried out in the presence of a conventional condensing agent such as carbodiimide compound [e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide N,N'-diisopropylcarbodiimide, N-ethyl-N'-(3-dimethylaminopropyl)carbodiimide]; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite, ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro- 1H-benzotriazole; combination of the carbodiimide compound mentioned above and 1-hydroxy-1H-benzotriazole or N-hydroxysuccinimide; or so-called Vilsmeier reagent prepared by the reaction of N,N-dimethylformamide with thionyl chloride, phosgene, trichloromethyl chloroformate, phosphorus oxychloride, etc.

The reaction may also be carried out in the presence of an inorganic or organic base such as an alkali metal bicarbonate, tri(lower)alkylamine, pyridine, N-(lower)alkylmorpholine, or N,N-di(lower)alkylbenzylamine.

The reaction temperature is not critical, and the reaction is usually carried out under cooling to warming.

When the imidazolyl group of the compound (IIa) is protected, the final product (I) may be prepared by elimination of the N-protective group of the reaction product of the compound (IIa) and the compound (III).

Elimination of the N-protective group is carried out in accordance with a conventional method such as hydrolysis or reduction.

The hydrolysis is preferably carried out in the presence of a base or an acid including Lewis acid.

Suitable base includes inorganic base and organic base such as alkali metal [e.g. sodium, potassium], alkaline earth metal [e.g. magnesium, calcium], hydroxide or carbonate or bicarbonate thereof, hydrazine, trialkylamine [e.g. trimethylamine, triethylamine], picoline, 1,5-diazabicyclo[4.3.0] non-5-ene, 1,4-diazabicyclo[2.2.2]octane, and 1,8-diazabicyclo[5.4.0]-undec-7-ene.

Suitable acid includes organic acid [e.g. formic acid, acetic acid, propionic acid, trichloroacetic acid, trifluoroacetic acid], inorganic acid [e.g. hydrochlorid acid, hydrobromic acid, sulfuric acid, hydrogen chloride, hydrogen bromide, hydrogen fluoride], and acid addition salt compound [e.g. pyridine hydrochloride].

Elimination using an acid such as trihaloacetic acid [e.g. trichloroacetic acid, trifluoroacetic acid]is preferably carried out in the presence of cation trapping agents [e.g. anisole, phenol].

The reaction is usually carried out in a solvent such as water, an alcohol [e.g. methanol, ethanol], methylene chloride, chloroform, tetrachloromethane, tetrahydrofuran, a mixture thereof or any other solvent which does not adversely influence the reaction. A liquid base or acid can be also used as a solvent.

The reaction temperature is not critical and the reaction is usually carried out under cooling to heating.

The reduction method applicable to the elimination includes chemical reduction and catalytic reduction.

Suitable reducing agents to be used in chemical reduction are combinations of metal [e.g. tin, zinc, iron] or metallic compound [e.g. chromium chloride, chromium acetate] and organic or inorganic acid [e.g. formic acid, acetic acid, propionic acid, trifluoroacetic acid, p-toluenesulfonic acid, hydrochloric acid, hydrobromic acid].

Suitable catalysts to be used for catalytic reduction are conventional ones such as platinum catalysts [e.g. platinum plate, spongy platinum, platinum black, colloidal platinum, platinum oxide, platinum wire], palladium catalysts [e.g. spongy palladium, palladium black, palladium oxide, palladium on carbon, colloidal palladium, palladium on barium sulfate, palladium on barium carbonate], nickel catalysts [e.g. reduced nickel, nickel oxide, Raney nickel], cobalt catalysts [e.g. reduced cobalt, Raney cobalt], iron catalysts [e.g. reduced iron, Raney iron], and copper catalysts [e.g. reduced copper, Raney copper, Ullman copper].

The reduction is usually carried out in a conventional solvent which does not adversely influence the reaction, such as water, methanol, ethanol, propanol, N,N-dimethylformamide, or a mixture thereof. Additionally, in case where the above-mentioned acids to be used in chemical reduction are liquids, they can be used also as a solvent. Further, a suitable solvent to be used in catalytic reduction may be the above-mentioned solvent, or other conventional solvents such as diethyl ether, dioxane, tetrahydrofuran, or a mixture thereof.

The reaction temperature of this reduction is not critical and the reaction is usually carried out under cooling to heating.

reactive derivative at the amino group or a salt thereof. This reaction can be carried out in substantially the same manner as the condensation in Process a, and the reaction mode and reaction conditions [e.g. reactive derivative, condensing agent, solvent, reaction temperature] of this reaction are to be referred to those as given for the condensation in Process a.

Step 2

The compound (I) or a salt thereof can be prepared by reacting a compound (II) or its reactive derivative at the carboxyl group or a salt thereof with a compound (III) or its reactive derivative at the amino group or a salt thereof, followed by elimination of the N-protective group as necessary.

This reaction can be carried out in substantially the same manner as the condensation in Process a, and the reaction mode and reaction conditions such as reactive derivative, condensing agent, solvent, and reaction temperature of this reaction are to be referred to those as given for the condensation in Process a.

In case where the imidazolyl group of the compound (V) is protected, the object compound (I) can be prepared by further eliminating the N-protective group of the reaction product of the compound (II) with the compound (III). This elimination reaction can be carried out in substantially the same manner as elimination in Process a, and the reaction mode and reaction conditions [e.g. base, acid, reducing agent, catalyst, solvent, reaction temperature] of this reaction are to be referred to those as given for elimination in Process a.

When preparing the compound (I) wherein $R^3$ is lower alkyl, a compound (V) wherein $R^3$ is lower alkyl may be used as a starting material, or as in the following Process c, a compound (Va) wherein $R^3$ is hydrogen may be used as a starting material, and lower alkyl may be introduced to $R^3$ Process b

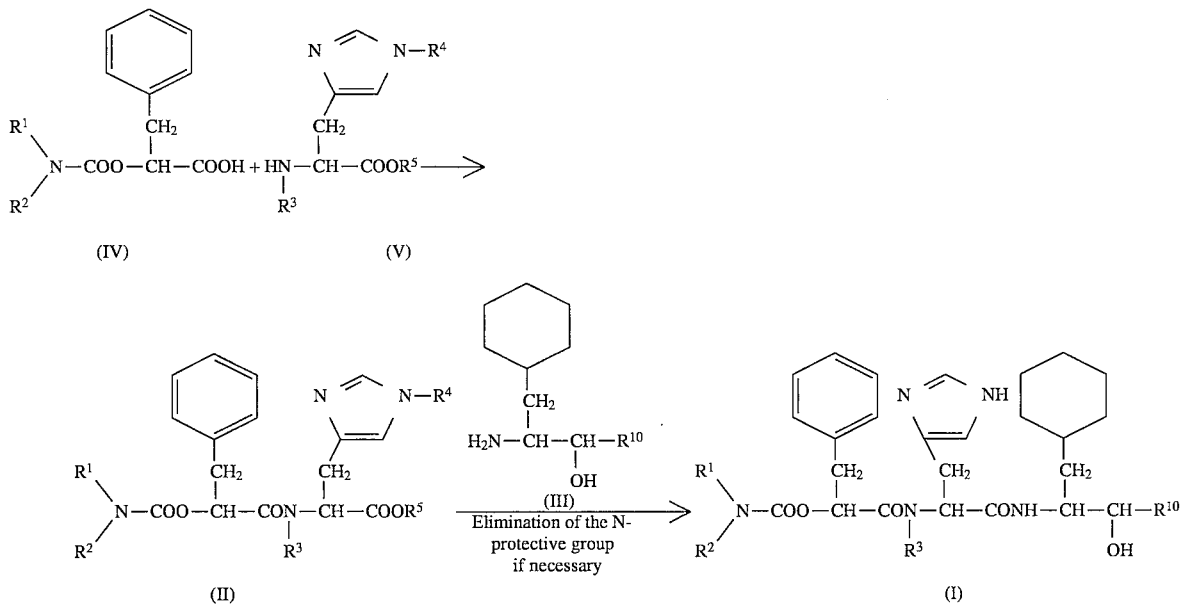

wherein $R^1$, $R^2$, $R^3$, $R^4$, $R^5$, and $R^{10}$ are as defined above.

Step 1

The compound (II) or a salt thereof can be prepared by reacting a compound (IV) or its reactive derivative at the carboxyl group or a salt thereof with a compound (V) or its by subjecting a compound (IIb) obtained by condensation of compounds (IV) and (Va) to alkylation.

Process c

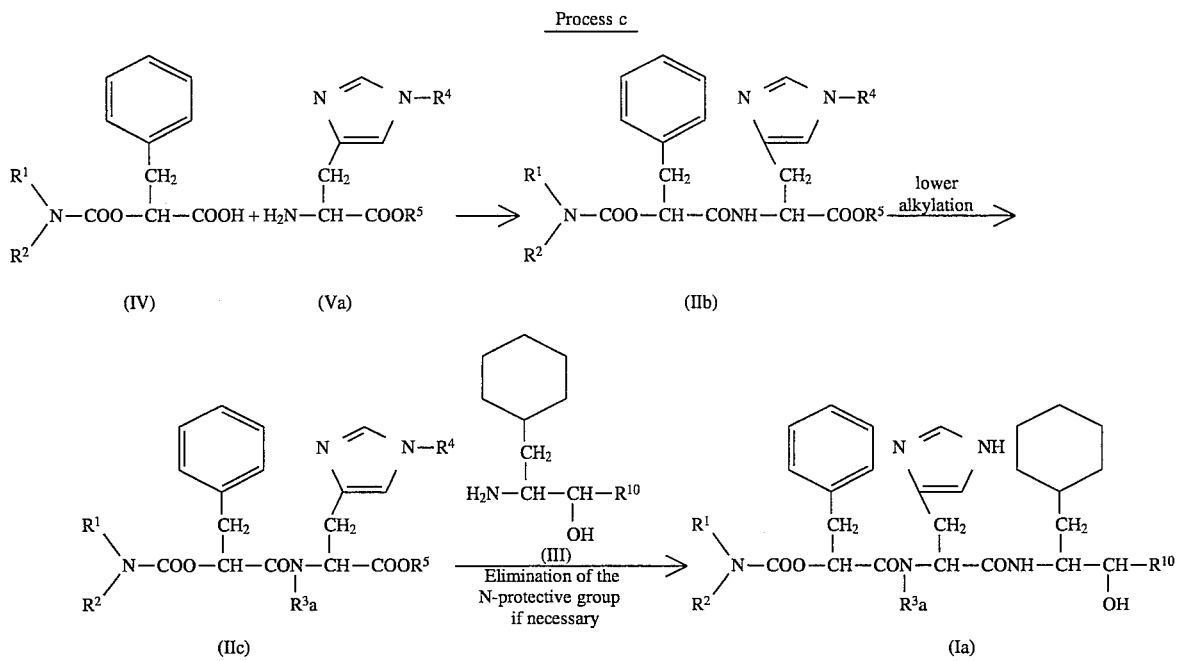

wherein $R^1$, $R^2$, $R^3a$, $R^4$, $R^5$, and $R^{10}$ are as defined above.

Step 1

The compound (IIb) or a salt thereof can be prepared by reacting a compound (IV) or its reactive derivative at the carboxyl group or a salt thereof with a compound (Va) or its reactive derivative at the amino group or a salt thereof. This reaction can be carried out in substantially the same manner as the condensation in Process a, and the reaction mode and reaction conditions such as reactive derivative, reducing agent, solvent, and reaction temperature of this reaction are to be referred to those as given for the condensation in Process a.

Step 2

The compound (IIc) or its salt can be prepared by subjecting a compound (IIb) or its salt to lower alkylation reaction.

Suitable lower alkylating agents to be used in this reaction is lower alkyl halide [e.g. methyl iodide, ethyl iodide, propyl iodide, butyl iodide, butyl chloride, pentyl chloride].

This reaction is usually carried out in the presence of a base such as alkali metal [e.g. sodium, potassium], alkaline earth metal [e.g. magnesium, calcium], hydride or hydroxide thereof, or alkali metal alkoxide [e.g. sodium methoxide, sodium ethoxide, potassium tert-butoxide].

This reaction is usually carried out in a conventional solvent such as water, alcohol [e.g. methanol, ethanol, propanol], tetrahydrofuran, dioxane, ethyl acetate, methylene chloride, N,N-dimethylformamide, dimethyl sulfoxide, diethyl ether, or any other organic solvent which does not adversely influence the reaction. In case where the above-mentioned lower alkylating agent is a liquid, it can be used also as a solvent.

The reaction temperature is not critical, and the reaction is usually carried out under cooling, at ambient temperature or under warming or heating.

Step 3

The compound (Ia) or a salt thereof can be prepared by reacting a compound (IIc) or its reactive derivative at the carboxyl group or a salt thereof with a compound (III) or its reactive derivative at the amino group or a salt thereof. This reaction can be carried out in substantially the same manner as the condensation in Process a, and the reaction mode and reaction conditions such as reactive derivative, condensing agent, solvent, and reaction temperature of this reaction are to be referred to those as given for the reduction in Process a.

When the imidazolyl group of the compound (Va) is protected, the final product (Ia) can be prepared by elimination of the N-protective group of the reaction product of compounds (IIc) and (III). This elimination can be carried out in substantially the same manner as the elimination in Process a, and the reaction mode and reaction conditions such as base, acid, reducing agent, catalyst, solvent, and reaction temperature of this reaction are to be referred to those as given for the elimination in Process a.

The starting compounds (III) and (IV) to be used in the processes of the invention can be respectively prepared by the following methods.

The compound (III) can be prepared by the method described in Tetrahedron:Asymmetry, Vol. 1, 375–378 (1990), which is to be described in the preparation examples to be mentioned later. The compound (IV) can be prepared by the method disclosed in EP-A-300189.

Some of the compounds of the formula (IV) can be synthesized also by the following reaction steps.

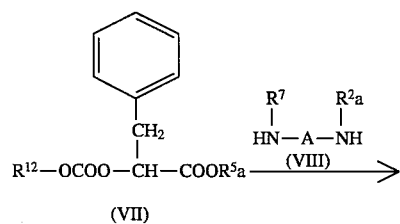

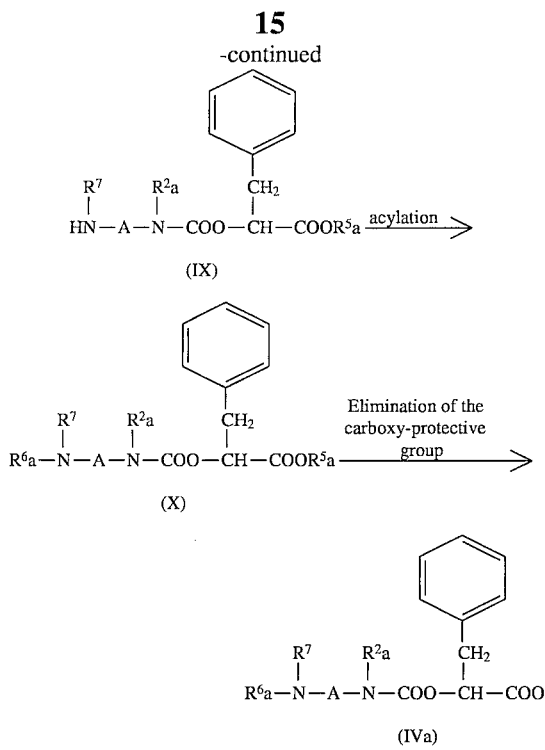

wherein $R^{12}$ is aryl which may have substituent(s), $R^2a$ is hydrogen or lower alkyl, $R^5a$ is a carboxy-protective group, $R^6a$ is acyl, A is lower alkylene, and $R^7$ is as defined above.

A compound (VII) is reacted with a compound (VIII) or a salt thereof to give a compound (IX) or a salt thereof. The obtained compound or salt is subjected to acylation to give a compound (X) or a salt thereof, which is then subjected to elimination of the carboxy-protective group to give a compound (IVa) or a salt thereof.

In the definition of $R^{12}$, "aryl which may have substituent(s)" preferably includes, for example, aryl as recited above and aryl substituted by a substituent such as nitro, with preference given to phenyl and nitrophenyl.

The reaction between the compound (VII) and the compound (VIII) is usually carried out in a conventional solvent such as water, alcohol (e.g. methanol, ethanol), acetone, dioxane, acetonitrile, chloroform, methylene chloride, ethylene chloride, tetrahydrofuran, ethyl acetate, N,N-dimethylformamide, or pyridine. Yet, the reaction can be also conducted in any other solvent so far as the solvent does not adversely affect the reaction.

While the reaction temperature is not subject to any particular limitation, it is usually conducted under cooling to warming.

The acylation is carried out by subjecting a compound (IX) or its reactive derivative at the amino group or a salt thereof to condensation with the compound (XI) of the formula $$R^6a\text{–}OH \tag{XI}$$

wherein $R^6a$ is acyl, or its reactive derivative at the carboxyl group or a salt thereof. This reaction can be carried out in substantially the same manner as the condensation in Process a, and the reaction mode and reaction conditions such as reactive derivative, condensing agent, catalyst, solvent, and reaction temperature of this reaction are to be referred to those as given for the reduction in Process a.

The elimination of the carboxy-protective group can be carried out in substantially the same manner as the elimination in Process a, and the reaction mode and reaction conditions such as base, acid, reducing agent, catalyst, solvent, and reaction temperature of this reaction are to be referred to those as given for the elimination in Process a.

The processes for preparing the compound (IVa) by the aforementioned steps is industrially advantageous in that they suppress production of byproducts, they afford high yields, and that the preparation cost is low.

The corresponding amino acid derivative (Ib) can be prepared by reacting the compound according to the Process b or Process c described above. When Process b is employed, the reaction proceeds as follows.

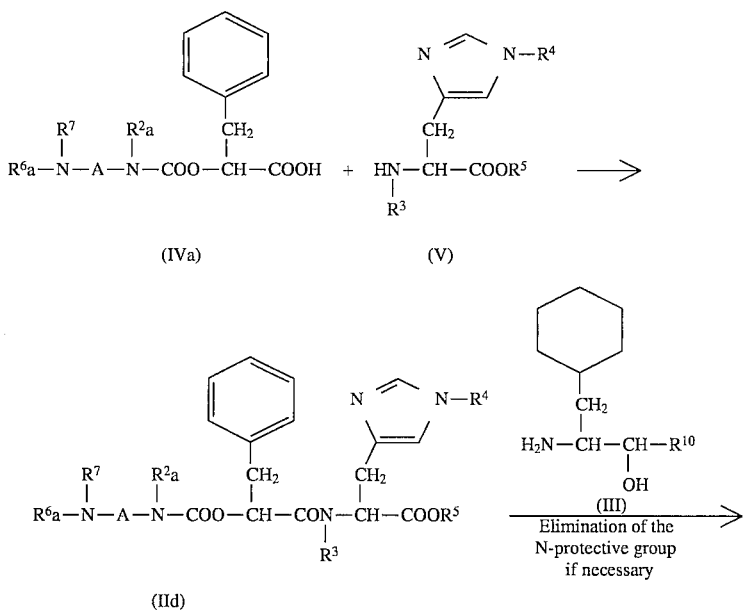

-continued

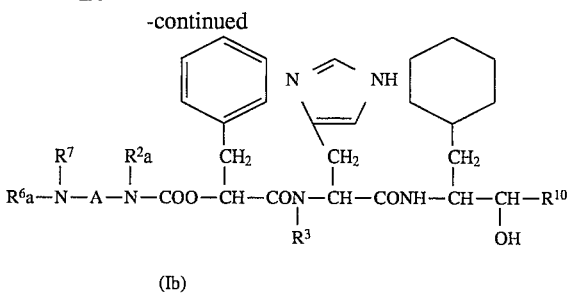

(Ib)

wherein $R^3$, $R^4$, $R^5$, $R^2a$, $R^6a$, $R^7$, $R^{10}$ and A are as defined above.

The compound (IId) or a salt thereof can be prepared by reacting a compound (IVa) or its reactive derivative at the carboxyl group or a salt thereof with a compound (V) or its reactive derivative at the amino group or a salt thereof. The obtained compound (IId) or its reactive derivative at the carboxyl group or a salt thereof is then reacted with a compound (III) or its reactive derivative at the amino group or a salt thereof, followed by elimination of the N-protective group as necessary to give the compound (Ib) or a salt thereof. Each step may be conducted according to Process b described above.

In the present invention, "$N^\alpha$-" is a substituent bound with the nitrogen atom of amino group of α-amino acid, and "$N^{im}$-" is a substituent bound with the nitrogen atom on imidazole ring.

EXAMPLES

The present invention is detailedly explained by way of examples in the following, but the invention is not limited to these examples.

Preparation Example 1

L-Phenylalanine (50 g), pulverized potassium carbonate (167 34 g), and sodium iodide (22.68 g) were added to N,N-dimethylacetamide (500 ml) while stirring, and water (25 ml) was added thereto. After elevating the temperature to 60° C., benzyl chloride (118.78 g) was dropwise added. After the dropwise addition, the mixture was vigorously stirred at 60°–65° C. for 6 hours. After the reaction, the reaction mixture was cooled to 20°–30° C., and water (750 ml) and ethyl acetate (500 ml) were added thereto for extraction. The ethyl acetate layer was separated, washed with water (500 ml), an aqueous solution of 10% sodium hydrogensulfite (500 ml×2), and water (500 ml), and concentrated to dryness under reduced pressure to give N,N-dibenzyl-L-phenylalanine benzyl ester (136.88 g) as a yellow, oily substance.

NMR (CDCl$_3$, δ): 2.94–3.19 (2H, m), 3.72 (1H, t, J=0.77 Hz), 3.73 (4H, AB system, J=7.86 Hz, 1.40 Hz), 5.17 (2H, AB system, J=2.51 Hz, 1.23 Hz), 6.98–7.35 (20H, m)

Preparation Example 2

N,N-Dibenzyl-L-phenylalanine benzyl ester (27.24 g) was dissolved in methanol (79.6 ml), and an aqueous solution of sodium hydroxide (sodium hydroxide 4.8 g, water 19.9 ml) was added thereto, followed by stirring under reflux for 1.5 hours. After the completion of the reaction, methanol was distilled away under reduced pressure, and water (99 ml) and ethyl acetate (99 ml) were added thereto for extraction. After separation of the ethyl acetate layer, it was washed with an aqueous solution of 5% sodium chloride (99 ml), and the ethyl acetate layer was concentrated to dryness under reduced pressure. Acetone (20 ml) was added to the concentrate, the inner temperature was raised to 45°–50° C., and 17.5% hydrochloric acid (50 ml) was dropwise added at said temperature. After the dropwise addition, acetone (30 ml) was dropwise added at said temperature. After stirring the mixture at said temperature for 30 minutes, the inner temperature was cooled to 20°–25° C. After stirring for 1 hour, the mixture was cooled to 5° C. or below, and stirred for 2 or more hours. The precipitated crystals were collected by filtration to give 21.19 g of N,N-dibenzyl-L-phenylalanine hydrochloride as white crystals.

melting point: 129°–156° C. (decomposition)

IR (Nujol): 3350, 2600, 1740, 1600, 1590 cm$^{-1}$

NMR (CDCl$_3$, δ): 2.93–3.29 (2H, m), 3.70–3.78 (1H, m), 3.77 (4H, AB system, J=2.70 Hz, 1.36 Hz), 6.69 (1H, bs), 7.03–7.32 (15H, m)

Preparation Example 3

N,N-Dibenzyl-L-phenylalanine hydrochloride (50 g) was dissolved in methylene chloride (500 ml), and an aqueous solution of sodium hydroxide (sodium hydroxide 6 g, water 500 ml) was added thereto. After stirring the mixture for 30 minutes, it was partitioned, and the organic layer was dried over magnesium sulfate and concentrated under reduced pressure to give N,N-dibenzyl-L-phenylalanine as an oily substance.

Pivaloyl chloride (44.90 g) was dissolved in tetrahydrofuran (1000 ml), and the solution was cooled to −20° C. To the solution was dropwise added the above-mentioned N,N-dibenzyl-L-phenylalanine and triethylamine (18.84 g) in tetrahydrofuran (500 ml) at −20°–15° C., followed by stirring at said temperature for 30 minutes.

A solution of isoamylmagnesium bromide separately prepared from magnesium (21.12 g), isoamyl bromide (150.03 g) in tetrahydrofuran (500 ml) was dropwise added thereto at −15°–0° C. over 2 hours. Immediately after the dropwise addition, acetic acid (50 ml) was dropwise added at said temperature, and the reaction mixture was poured into an aqueous solution of 20% ammonium chloride (500 ml). Toluene (500 ml) and 7% hydrochloric acid (500 ml) were added thereto for partition. The organic layer was washed with 7% hydrochloric acid (500 ml), an aqueous solution of 5% sodium hydrogencarbonate (500 ml), and saturated brine (500 ml), sequentially. The organic layer was dried over magnesium sulfate, and concentrated under reduced pressure to give 100.2 g of 2(S)-(N,N-dibenzylamino)-1-phenyl-3-oxo-6-methylheptane as a yellow, oily substance.

IR (Neat): 2700–3150, 1950, 1870, 1805, 1710, 1600, 1450 cm$^{-1}$

NMR (CDCl$_3$, δ): 0.80–1.43 (4H, m), 2.05–2.60 (2H, m), 2.86–3.22 (2H, m), 3.53–3.67 (1H, m), 3.70 (4H, AB system, J=3.71 Hz, 1.36 Hz), 7.08–7.33 (15H, m)

Preparation Example 4

2(S)-(N,N-Dibenzylamino)-1-phenyl-3-oxo-6-methylheptane (100 g) was dissolved in a mixture of methanol (500 ml) and tetrahydrofuran (500 ml), and the solution was cooled to −20° C. To the solution was portionwise added sodium borohydride (63 g) at said temperature. After the completion of the reaction, the reaction mixture was concentrated under reduced pressure, and ethyl acetate (500 ml) and water (500 ml) were added to the residue for extraction. The water layer was re-extracted with ethyl acetate (250 ml). The combined organic layer was washed with saturated brine (500 ml), and the organic layer was concentrated. Water (100 ml) was added to the residual oily substance, and azeotropic distillation was performed. After 8 times of azeotropic distillation, toluene (100 ml) was added. Additional azeotropic distillation gave 2(S)-(N,N-dibenzylamino)-1-phenyl-3(S)-hydroxy-6-methylheptane (56.8 g).

IR (Nujol): 3400, 3350, 1950, 1890, 1810, 1600, 1590 cm$^{-1}$

NMR (CDCl$_3$, δ): 0.74 (6H, d, J=0.64 Hz), 0.95–1.43 (5H, m), 2.81–2.92 (1H, m), 2.88 (2H, ABX system, J=6.75 Hz, 1.40 Hz, 0.61 Hz), 3.55 (1H, dt, J=0.63 Hz, 0.26 Hz), 3.64 (4H, AB system, J=10.60 Hz, 1.32 Hz), 4.49 (1H, bs), 7.19–7.36 (15H, m)

Preparation Example 5

2(S)-(N,N-Dibenzylamino)-1-phenyl-3(S)-hydroxy-6-methylheptane (25 g) was dissolved in methanol (250 ml), and 10% palladium-carbon (1.25 g) suspended in water (10 ml) was added thereto. Then, ammonium formate (15.70 g) was added thereto, and the mixture was stirred at ambient temperature for 5 hours, followed by concentration under reduced pressure. The residue was dissolved in methylene chloride and washed with water. The organic layer was dried over magnesium sulfate and concentrated under reduced pressure to give 14.0 g of 2(S)-amino-1-phenyl-3(S)-hydroxy-6-methylheptane.

IR (Nujol): 3350, 3300, 3000, 2730, 1600, 1500 cm$^{-1}$

NMR (CDCl$_3$, δ): 0.90 (6H, d, J=0.63 Hz), 1.16–1.63 (5H, m), 1.85 (2H, bs), 2.84–2.97 (2H, m), 3.30–3.38 (1H, m), 7.18–7.36 (5H, m)

Preparation Example 6

2(S)-Amino-1-phenyl-3(S)-hydroxy-6-methylheptane (13 g) was dissolved in acetic acid (130 ml), and thereto was added platinum oxide (1.3 g) to conduct catalytic reduction at medium pressure (4 atmospheric pressure). The reaction mixture was heated to 45° C.

After the reaction, the catalyst was filtered off, and the filtrate was concentrated under reduced pressure. The residue was dissolved in methylene chloride and washed with an aqueous solution of 5% sodium hydrogencarbonate. The organic layer was dried over magnesium sulfate, and the solvent was evaporated under reduced pressure to give 11.25 g of 2(S)-amino-1-cyclohexyl-3(S)-hydroxy-6-methylheptane.

IR (Nujol): 3410, 3350, 3300, 2900, 2700, 1600 cm$^{-1}$

NMR (CDCl$_3$, δ): 0.90 (6H, d, J=0.8 Hz), 0.77–1.74 (21H, m), 2.60–2.70 (1H, m), 3.13–3.21 (1H, m)

Preparation Example 7

L-Tartaric acid (6.60 g) was dissolved by heating (70°–75° C.) in a mixture of isopropyl alcohol (90 ml) and water (10 ml), and 2(S)-amino-1-cyclohexyl-3(S)-hydroxy-6-methylheptane (10 g) in isopropyl alcohol (100 ml) was dropwise added thereto. After the dropwise addition, the reaction mixture was cooled, and the precipitated crystals were collected by filtration to give 11.67 g of L-tartaric acid salt of 2(S)-amino-1-cyclohexyl-3(S)-hydroxy-6-methylheptane.

Preparation Example 8

Methyl 2(S)-amino-3-cyclohexylpropionate hydrochloride (150 g) was dissolved in N,N-dimethylformamide (1200 ml). Thereto was added pulverized potassium carbonate (330.7 g), and benzyl bromide (254.6 g) was dropwise added to the obtained suspension while stirring. After the dropwise addition, the inner temperature was raised to 50° C., and the reaction mixture was stirred at said temperature for 9 hours. The reaction mixture was cooled and filtered. Water (600 ml) and diisopropyl ether (600 ml) were added to the filtrate for partition, and the organic layer was separated. The water layer was re-extracted with diisopropyl ether (300 ml), and the combined organic layer was washed with 5% hydrochloric acid (600 ml), 5% aqueous sodium hydrogencarbonate (600 ml), and 25% aqueous sodium chloride sequentially and dried over magnesium sulfate. The solvent was distilled away to give 204.6 g of methyl 2(S)-(N,N-dibenzylamino)-3-cyclohexylpropionate.

NMR (CDCl$_3$, δ): 0.58–1.69 (13H, m), 3.37–3.44 (1H, m), 3.70 (4H, AB system, J=8.17 Hz, 1.38 Hz), 3.74 (3H, s), 7.17–7.48 (10H, m)

Preparation Example 9

Methyl 2(S)-(N,N-dibenzylamino)-3-cyclohexylpropionate (200 g) was dissolved in methanol (1 l), and thereto was added an aqueous solution of sodium hydroxide (sodium hydroxide 32.8 g, water 200 ml), followed by refluxing for 6 hours. After the completion of the reaction, the reaction mixture was concentrated, and ethyl acetate (1 l) was added to the residue for dissolution, after which water (400 ml) was added for partition. The organic layer was separated, washed with an aqueous solution of 10% citric acid (400 ml) and saturated brine (400 ml), and dried over magnesium sulfate. The solvent was evaporated under reduced pressure to give 191.1 g of 2(S)-(N,N-dibenzylamino)-3-cyclohexylpropionic acid.

NMR (CDCl$_3$, δ): 0.69–1.64 (13H, m), 3.45 (1H, t, J=0.70 Hz), 3.75 (4H, AB system, J=2.46 Hz, 1.36 Hz), 7.21–7.38 (10H, m), 7.90 (1H, bs)

Preparation Example 10

Pivaloyl chloride (5.15 g) was dissolved in tetrahydrofuran (30 ml), and the solution was cooled to −30° C. A solution of 2(S)-(N,N-dibenzylamino)-3-cyclohexylpropionic acid (5.0 g) and triethylamine (4.32 g) in tetrahydrofuran (20 ml) was dropwise added thereto at said temperature over 15 minutes. After the dropwise addition, the mixture was stirred at 20° C. for 1 hour.

The reaction mixture was again cooled to −50° C., and a solution of isoamylmagnesium bromide in tetrahydrofuran prepared from isoamyl bromide (21.49 g), magnesium (3.46 g), and tetrahydrofuran (50 ml) was dropwise added at said temperature over 15 minutes. After the dropwise addition, the mixture was stirred at said temperature for 30 minutes, at 15° C. for 30 minutes, and at 25° C. for 1 hour. The reaction mixture was poured into an aqueous solution of 20% ammonium chloride (100 ml). Toluene (100 ml) was added thereto, and the pH of the mixture was adjusted to 6–7 with 7% hydrochloric acid, followed by separation of the organic layer. The organic layer was washed with 7% hydrochloric acid (100 ml,×2), an aqueous solution of 5% sodium hydrogencarbonate (100 ml), and saturated brine (100 ml), and dried over magnesium sulfate. The solvent was evaporated under reduced pressure to give 9.41 g of 2(S)-(N,N-dibenzylamino)-1-cyclohexyl-3-oxo-6-methylheptane.

NMR (CDCl$_3$, δ): 0.85 (6H, dd, J=0.63 Hz, 0.09 Hz), 1.13–1.74 (16H, m), 2.24–2.61 (2H, m), 3.32 (1H, q, J=0.46 Hz), 3.61 (4H, AB system, J=3.48 Hz, 1.37 Hz), 7.19–7.36 (10H, m)

Preparation Example 11

2(S)-(N,N-Dibenzylamino)-1-cyclohexyl-3-oxo-6-methylheptane (2 g) was dissolved in a mixture of methanol (20 ml) and tetrahydrofuran (20 ml), and the solution was cooled to −20° C. Sodium borohydride (0.2 g) was added to the reaction mixture while keeping the temperature at −20° C. After the addition, the reaction was carried out at said temperature for 1.5 hours.

Upon completion of the reaction, water (50 ml) was added to the reaction mixture, and methylene chloride (50 ml) was added thereto for extraction. After the methylene chloride layer was dried over anhydrous magnesium sulfate, the solvent was evaporated under reduced pressure to give 2.01 g of 2(S)-(N,N-dibenzylamino)- 1-cyclohexyl-3(S)-hydroxy-6-methylheptane.

NMR (CDCl$_3$, δ): 0.85 (6H, AB system, J=0.64 Hz, 0.21 Hz), 0.79–1.74 (18H), 2.46–2.56 (1H, m), 3.37–3.49 (1H, m), 3.62 (4H, AB system, J=8.76 Hz, 1.35 Hz), 4.48 (1H, bs), 7.16–7.37 (10H, m)

Preparation Example 12

2(S)-(N,N-Dibenzylamino)-1-cyclohexyl-3(S)-hydroxy-6-methylheptane (5 g) was dissolved in methanol (50 ml). Ammonium formate (6.18 g) and then 10% palladium-carbon (50% wet, 0.5 g) were added thereto, and the mixture was vigorously stirred at room temperature. After the completion of the reaction, the reaction mixture was filtered, and the filtrate was concentrated under reduced pressure. Ethyl acetate and water were added to the concentrated residue for extraction. The organic layer was washed with saturated brine and dried over anhydrous magnesium sulfate. The solvent was evaporated under reduced pressure to give 4.13 g of 2(S)-amino-1-cyclohexyl-3(S)-hydroxy-6-methylheptane.

NMR (CDCl$_3$, δ): 0.90 (6H, d, J=0.8Hz), 0.77–1.74 (21H, m), 2.60–2.70 (1H, m), 3.13–3.21 (1H, m)

Example 1

L-Histidine (100 g) was suspended in methylene chloride (2.0 l). Dichlorodimethylsilane (83.2 g) was added at an inner temperature of 20°–30° C., and the mixture was refluxed under heating for 3 hours. Triethylamine (66.5 g) was dropwise added over 15–30 minutes while refluxing, and the mixture was further refluxed under heating for 30 minutes.

After silylation, the reaction mixture was cooled to an inner temperature of 20°–30° C., and a solution of trityl chloride (188.6 g) in methylene chloride (300 ml) was dropwise added at said temperature over 1 hour. After the dropwise addition, the reaction is carried out at said temperature for 1 hour.

After tritylation, the reaction mixture was concentrated under reduced pressure, and methanol (200 ml) was added to the residue. After stirring the mixture for 15 minutes, water (1 l) was dropwise added at an inner temperature of 20°–30° C. over 30 minutes. After the dropwise addition, the pH of the mixture was adjusted to 6.5–7.5 with triethylamine. Then, precipitated crystals were filtered off at said temperature. The obtained crystals were washed with water (400 ml) and methylene chloride (500 ml), sequentially and dried in vacuo overnight to give 192.3 g of $N^{im}$-trityl-L-histidine (yield 75%).

NMR (DMSO-d$_6$, δ): 6.76 (1H, s), 7.08–7.13 (6H, m), 7.29 (1H, s), 7.37–7.43 (9H, m)

Example 2

Cyclohexylamine salt of 2(S)-[N-Methyl-N-[2-{N-(morpholinocarbonyl)-N-methylamino}ethyl]aminocarbonyloxy]-3-phenylpropionic acid (100 g) in methylene chloride (1000 ml) was cooled to an inner temperature of 10° C. Thereto was added 5% hydrochloric acid (500 ml), and the mixture was stirred at an inner temperature of 10°–15° C. for 10 minutes to give a free compound. The mixture was left standing, and the methylene chloride layer was separated and washed with 20% aqueous sodium chloride (500 ml). The methylene chloride layer obtained was dried over magnesium sulfate and filtered to give a solution of the free compound in methylene chloride.

To this solution was added N-hydroxysuccinimide (25.7 g), and the solution was cooled to an inner temperature of 0° C. Then, a solution of N,N'-dicyclohexylcarbodiimide (46.1 g) in methylene chloride (200 ml) was added at an inner temperature of 5° C. or below, and the reaction was carried out at an inner temperature of 0°–5° C. for 2 hours. After the completion of the reaction, precipitated N,N'-dicyclohexylurea was filtered off and washed with methylene chloride (200 ml). The combined filtrate and washing solution was washed with an aqueous solution of 5% citric acid (500 ml) and water (500 ml). The methylene chloride layer was separated, dried over magnesium sulfate and concentrated under reduced pressure to the residue amount (100 ml) to give a solution of active ester.

On the other hand, 1,1,1,3,3,3-hexamethyldisilazane (44.6 g), $N^{im}$-trityl-L-histidine (85.4 g), and trimethylsilyl chloride (33.1 g) were added to methylene chloride (1000 ml), and silylation was conducted while refluxing under heating for 1 hour.

After the completion of the reaction, the reaction mixture was cooled to an inner temperature of 30° C. or below. The aforementioned solution of active ester was added, and condensation was carried out at 20°–30° C. for 1 hour.

After the condensation, water (1000 ml) was added to the reaction mixture. The reaction mixture was stirred and allowed to stand, and the methylene chloride layer was separated. The methylene chloride layer was washed with an aqueous solution of 5% citric acid (1000 ml) and water (1000 ml). The methylene chloride layer was separated and concentrated to dryness to give 174.6 g of $N^{\alpha}$-[2(S)-[N-methyl-N-[2-{N-(morpholinocarbonyl)-N- methylamino}ethyl]aminocarbonyloxy]-N$^{im}$-trityl-L-histidine.

NMR (CDCl$_3$, δ): 2.73–2.97 (8H, m), 3.01–3.61 (14H, m), 4.46 (1H, br), 5.18 (1H, br), 6.75–6.90 (1H, m), 7.09–7.34 (20H, m), 7.40–7.55 ( 1H, m)

Example 3

N$^α$-[2(S)-[N-Methyl-N-[2-{N-(morpholinocarbonyl)-N-methylamino}ethyl]aminocarbonyloxy]-3-phenylpropionyl]-N$^{im}$-trityl-L-histidine (100 g) was dissolved in tetrahydrofuran (1000 ml), and thereto was added water (1.0 g). The mixture was cooled to an inner temperature of −10° C., and sodium hydride (60%, 11.4 g) was added thereto. Methyl iodide (110.2 g) was dropwise added at an inner temperature of not more than −5° C., and the mixture was allowed to react at an inner temperature of 0°–5° C. for 3 hours. After the completion of the reaction, the reaction mixture was poured into a mixture of an aqueous solution of 5% citric acid (500 ml) and methylene chloride (500 ml), and the mixture was stirred and allowed to stand, after which the organic layer was separated. The organic layer was washed with water (500 ml), and concentrated to dryness under reduced pressure. Ethyl acetate (1000 ml) and an aqueous solution of 5% sodium bicarbonate (2000 ml) were added to the concentrate for dissolution, and the mixture was stirred and allowed to stand. Thereafter, the water layer was separated. The separated water layer was adjusted to pH 4–4.5 with citric acid, and added with methylene chloride (2000 ml) to extract the object compound. The methylene chloride layer was separated, washed with water (500 ml), dried over magnesium sulfate, and concentrated to dryness under reduced pressure to give 94.7 g of N$^α$-[2(S)-[N-methyl-N-[2-{N-(morpholinocarbonyl)-N-methylamino}ethyl]aminocarbonyloxy]-3-Phenylpropionyl]-N$^α$-methyl-N $^{im}$-trityl-L-histidine (yield 93%).

NMR (CDCl$_3$, δ): 2.71–2.90 (8H, m), 3.03–3.62 (17H, m), 5.29–5.34 (2H, m), 6.60–6.80 (1H, m), 7.02–7.38 (20H, m), 7.50–7.75 (1H, m)

Example 4

L-Tartaric acid salt of 2(S)-amino-1-cyclohexyl-3(S)-hydroxy- 6-methylheptane (48.0 g) was added to methylene chloride (400 ml), and 25% aqueous ammonia (150 ml) and water (50 ml) were added thereto while stirring to give a free compound. After allowing to stand, the methylene chloride layer was separated and washed with water (150 ml). The separated methylene chloride was dried over magnesium sulfate and concentrated to dryness under reduced pressure. To the concentrate were added tetrahydrofuran (800 ml), N$^α$-[2(S)-[N-methyl-N-[2-{N-(morpholinocarbonyl)-N-methyl-amino}ethyl]aminocarbonyloxy]-3-phenylpropionyl]-N$^α$-methyl-N $^{im}$-trityl-L-histidine (100.0 g), and 1-hydroxy-1H-benzotriazole (20.6 g). After dissolution, the mixture was cooled to −5° C.—10° C. N,N'-Dicyclohexylcarbodiimide (28.8 g) and N-methylmorpholine (6.43 g) were added thereto and reaction was carried out at said temperature for 24 hours. After the completion of the reaction, the precipitated N,N'-dicyclohexylurea was filtered off and washed with ethyl acetate (50 ml). To the combined filtrate and washing solution were added ethyl acetate (1000 ml) and an aqueous solution of 5% citric acid (1000 ml), and the mixture was stirred and allowed to stand, after which the organic layer was separated. The obtained organic layer was washed with 25% aqueous sodium chloride, a cooled aqueous solution of 5% sodium hydroxide, and 25% aqueous sodium chloride (each 1000 ml) sequentially. The organic layer was concentrated to dryness under reduced pressure and subjected to purification by silica gel column chromatography (developing solvent:methylene chloride and a mixture of 3% methanol and 97% methylene chloride) to give 114.1 g of 2(S)-[N$^α$-[2(S)-[N-methyl-N-[2-{N-(morpholinocarbonyl)-N-methylamino}ethyl]aminocarbonyloxy]-3-phenylpropionyl]-N$^α$-methyl-N$^{im}$-trityl-L-histidyl]amino-1-cyclohexyl- 3(S)-hydroxy-6-methylheptane (yield after the purification 91%).

NMR (CDCl$_3$, δ): 0.83 (6H, dd, J=6.0 Hz, 6.0 Hz ), 1.15–1.63 (18H, m), 2.74–3.62 (21H, m), 4.05–4.15 (1H, m), 5.02–5.11 (1H, m), 6.60–6.80 (1H, m), 7.03 (5H, m), 7.26 (16H, m)

Example 5

2(S)-[N$^α$-[2(S)-[N-Methyl-N-[2-{N-(morpholinocarbonyl)-N-methylamino}ethyl]aminocarbonyloxy]-3-phenyl-propionyl]-N$^α$-methyl-N $^{im}$-trityl-L-histidyl]amino-1-cyclohexyl-3(S)-hydroxy-6-methylheptane (100 g) was dissolved in 50% water-containing acetic acid (1000 ml), and detritylation was performed at an inner temperature of 50°–55° C. for 2 hours. After the completion of the reaction, the mixture was cooled to an inner temperature of 20°–30° C. and ethyl acetate (1000 ml) was added thereto. The mixture was adjusted to pH 7.8–8.0 with 25% aqueous ammonia, stirred, and allowed to stand, after which the organic layer was separated. To the organic layer was added an aqueous solution of 10% citric acid (1000 ml). The mixture was stirred and allowed to stand. The citric acid layer was separated, and the organic layer was re-extracted with an aqueous solution of 10% citric acid (500 ml). The combined citric acid layer was washed with ethyl acetate (500 ml). To the separated citric acid layer was added ethyl acetate (500 ml) and the mixture was adjusted to pH 7.8–8.0 with 25% aqueous ammonia. The mixture was stirred and allowed to stand, whereafter the organic layer was separated. The separated organic layer was washed with 20% aqueous sodium chloride (500 ml), dried over magnesium sulfate, and concentrated to dryness under reduced pressure to give 70.1 g of 2(S)-[N$^α$-[2(S)-[N-methyl-N-[2-{N-(morpholinocarbonyl)-N-methylamino}-ethyl]aminocarbonyloxy]-3-phenylpropionyl]-N$^α$-methyl-L-histidyl]amino-1-cyclohexyl-3(S)-hydroxy-6-methylheptane (yield 93%).

Example 6

2(S)-[N$^α$-[2(S)-[N-Methyl-N-[2-{N-(morpholinocarbonyl)-N-methylamino}ethyl]aminocarbonyloxy]-3-phenyl-propionyl]-N$^α$-methyl-L-histidyl]amino-1-cyclohexyl-3(S)-hydroxy-6-methylheptane (100 g) was dissolved in ethyl acetate (1000 ml), and filtered for clarification through a 0.6μ filter. After washing with ethyl acetate (200 ml), the filtrate and the washing solution were combined. Thereto was added 4N-hydrochloric acid/ethyl acetate solution (33.2 ml) at an inner temperature of 20°–30° C., and the mixture was stirred for 20 minutes. The mixture was concentrated to dryness under reduced pressure, and ethyl acetate (800 ml) and acetone (160 ml) were added to the residue. After dissolution, n-hexane (800 ml) was dropwise added at an inner temperature of 55°–60° C. over 30 minutes. After the dropwise addition, seed crystal (0.05 g) was added, and the mixture was stirred at said temperature for 13.5 hours to allow thorough precipitation of crystals. The mixture was cooled to an inner temperature of 20°–30° C., stirred at said temperature for 1 hour, and the resulting crystals were collected by filtration. The crystals were washed with a mixture of ethyl acetate-n-hexane (100 ml–200 ml) and dried in vacuo overnight to give 82.2 g of 2(S)-[N$^\alpha$-[2(S)-[N-methyl-N-[2-{N-(morpholinocarbonyl)-N-methylamino}ethyl]aminocarbonyloxy]-3-phenylpropionyl]-N$^\alpha$-methyl-L-histidyl]amino- 1-cyclohexyl-3(S)-hydroxy-6-methylheptane hydrochloride (yield 78%, total yield from N$^{im}$-trityl-L-histidine 68%).

NMR (D$_2$O, δ): 0.83 (6H, d, J=6.0 Hz), 1.04–1.82 (18H, m), 2.64–3.88 (24H, m), 3.90–4.05 (1H, m), 5.12–5.20 (1H, m), 7.2–7.4 (6H, m), 8.61 (1H, s)

Example 7

To methyl 2(S)-hydroxy-3-phenylpropionate (5.0 g) and pyridine (8.78 g) in methylene chloride (50 ml) was dropwise added phenyl chlorocarbonate (4.78 g) under cooling at 0°–10° C. over 30 minutes. After the dropwise addition, the mixture was stirred at said temperature for 60 minutes, washed with 10% hydrochloric acid and water, dried over magnesium sulfate, and concentrated to dryness under reduced pressure. As a result, 9.51 g of methyl 2(S)-phenoxycarbonyloxy-3-phenylpropionate was obtained as a pale yellow, oily substance.

NMR (CDCl$_3$, δ): 3.1–3.3 (2H, m), 3.7 (3H, s), 5.2 (1H, dd, J=8.7 Hz, 4.8 Hz), 7.0–7.4 (10H, m)

Example 8

To N,N'-dimethylethylenediamine (7.93 g) in N,N-dimethylformamide (27 ml) was dropwise added methyl 2(S)-phenoxycarbonyloxy- 3-phenylpropionate (9.0 g) in N,N-dimethylformamide (9 ml) under cooling at −5°–10° C. over 30 minutes. After the dropwise addition, the mixture was stirred at said temperature for 60 minutes and poured into a mixture of ethyl acetate and 20% aqueous sodium chloride for partition. The water layer was re-extracted with ethyl acetate, the organic layer was combined, and 5% hydrochloric acid was added thereto for partition. The water layer was washed with ethyl acetate, added with methylene chloride, and adjusted to pH 9.0 with an aqueous solution of 24% sodium hydroxide. The organic layer was separated, washed with 20% aqueous sodium chloride, and dried over magnesium sulfate. The solvent was evaporated under reduced pressure to give 8.64 g of methyl 2(S)-[N-( 2-methylaminoethyl)-N-methylaminocarbonyloxy]-3-phenylpropionate (yield 97.9%).

NMR (CDCl$_3$, δ): 2.5 (3H, d, J=4.81 Hz), 2.6–2.8 (2H, m), 2.9 (3H, s), 3.0–3.2 (2H, m), 3.2–3.5 (2H, m), 3.7 (3H, s), 5.2 (1H, m), 7.1–7.3 (5H, m)

Example 9

Methyl 2(S)-[N-(2-methylaminoethyl)-N-methylaminocarbonyloxy]- 3-phenylpropionate (8.0 g) was dissolved in methylene chloride (40 ml), and triethylamine (4.13 g) was added thereto under cooling. Thereto was dropwise added morpholinocarbonyl chloride (4.07 g) at 0°–10° C. over 30 minutes. After the dropwise addition, the mixture was stirred at said temperature for 60 minutes, washed with 5% hydrochloric acid, water, an aqueous solution of 6% sodium hydrogencarbonate, and water in this order, and the solvent was evaporated under reduced pressure to give 9.83 g of methyl 2(S)-[N-methyl-N-[2-{N-(morpholinocarbonyl)-N-methylamino}ethyl]aminocarbonyloxy]-3-phenylpropionate (yield 88.8%).

Example 10

To methyl 2(S)-[N-methyl-N-[2-{N-(morpholinocarbonyl)-N-methylamino}ethyl]aminocarbonyloxy]-3-phenylpropionate (9.0 g) dissolved in methanol (27 ml) was dropwise added an aqueous solution of sodium hydroxide (sodium hydroxide 1.77 g/water 9 ml) under cooling at 0°–5° C. over 30 minutes. After the dropwise addition, the mixture was stirred at said temperature for 60 minutes, and washed with methylene chloride. Methylene chloride was added to the water layer, and the mixture was adjusted to pH 1.0 with 6N hydrochloric acid and partitioned. The organic layer was washed with water, dried over magnesium sulfate, and concentrated to dryness under reduced pressure. Ethyl acetate (104 ml) was added to the concentrate and the mixture was heated to 40°–50° C. for dissolution. Cyclohexylamine (1.75 g) was added thereto to cause precipitation of crystals. The mixture was cooled to 0° C. or below, and the precipitated crystals were collected by filtration to give 8.13 g of cyclohexylamine salt of 2(S)-[N-methyl-N-[2-{N-(morpholinocarbonyl)-N-methylamino}ethyl]aminocarbonyloxy]-3-phenylpropionic acid (yield 74.7%).

The properties of the free compound of the compound obtained were identical with those of the compound of EP-A-300189.

According to the process of the present invention, the total yield from the starting material N$^{im}$-trityl-L-histidine was 68%, thus showing improvement in yield as compared with conventional methods. Preparation of the final product (I) at high yields from less expensive starting material L-histidine results in drastic reduction of preparation cost, which in turn proves industrial usefulness of the preparation process of the invention.

The compound (II) is a novel compound which is useful as a synthetic intermediate for the preparation process of the invention.

What is claimed is:

1. A compound of the formula

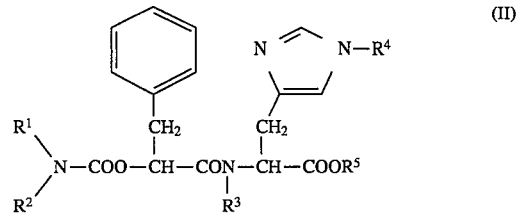

(II)

wherein

R$^1$ is lower alkyl which may be substituted by a substituent selected from the group consisting of acyl, hydroxyl, lower alkoxy, aryl, lower alkylthio and a group of the formula

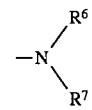

wherein R$^6$ is hydrogen or acyl, and R$^7$ is hydrogen or lower alkyl; aryl; or amino which may be substituted by substituent(s) selected from the group consisting of lower alkyl and acyl;

R$^2$ is hydrogen or lower alkyl; or R$^1$ and R$^2$ together with the attached nitrogen atom form a heterocyclic group which may be substituted by substituent(s) selected from the group consisting of lower alkyl, hydroxy(lower)alkyl, lower alkoxy(lower)alkyl, acyl(lower)alkyl, oxo and acyl;

$R^3$ is hydrogen or lower alkyl;

$R^4$ is hydrogen or an N-protective group; and $R^5$ is hydrogen or a carboxy-protective group; or a salt thereof.

2. The compound of claim 1, wherein $R^1$ is lower alkyl substituted by a group of the formula

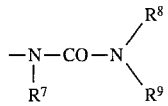

wherein $R^7$ is hydrogen or lower alkyl, and $R^8$ and $R^9$ together with the attached nitrogen atom form a heterocyclic group which may be substituted by lower alkyl;

$R^2$ is lower alkyl; and $R^5$ is hydrogen or lower alkyl.

3. The compound of claim 2 which is selected from the group consisting of $N^{\alpha}$-[2(S)-[N-methyl-N-[2-{N-(morpholinocarbonyl)-N-methylamino}ethyl]aminocarbonyloxy]-3-phenylpropionyl]-$N^{im}$-trityl-L-histidine and $N^{\alpha}$-[2(S)-[N-methyl-N-[2-{N-(morpholinocarbonyl)-N-methylamino}ethyl]aminocarbonyloxy]-3-phenylpropionyl]-$N^{\alpha}$-methyl-$N^{im}$-trityl-L-histidine.

* * * * *